United States Patent
Lubock et al.

(10) Patent No.: US 8,057,379 B2
(45) Date of Patent: *Nov. 15, 2011

(54) TREATMENT OF A BODY CAVITY

(75) Inventors: Paul Lubock, Laguna Niguel, CA (US); Michael L. Jones, San Clemente, CA (US)

(73) Assignee: Senorx, Inc., Irvine, CA (US)

( * ) Notice: Subject to any disclaimer, the term of this patent is extended or adjusted under 35 U.S.C. 154(b) by 930 days.

This patent is subject to a terminal disclaimer.

(21) Appl. No.: 12/012,744

(22) Filed: Jan. 31, 2008

(65) Prior Publication Data

US 2008/0188705 A1    Aug. 7, 2008

Related U.S. Application Data

(62) Division of application No. 11/283,236, filed on Nov. 18, 2005, now Pat. No. 7,413,539.

(51) Int. Cl.
*A61N 5/00* (2006.01)

(52) U.S. Cl. .......................................................... 600/3

(58) Field of Classification Search ................. 600/1–9, 600/30, 407, 424, 427; 604/19–21, 27–28, 604/48, 73, 93.01, 95.03, 96.01, 101.01–101.05, 604/102.01–102.03, 103.05–103.07, 158–159, 604/164.01, 164.08, 263–264, 506–511, 604/514–517; 606/1, 32–34, 41; 607/1–2, 607/100–101, 122, 154–156

See application file for complete search history.

(56) References Cited

U.S. PATENT DOCUMENTS

| | | | |
|---|---|---|---|
| 3,324,847 A | 6/1967 | Zoumboulis | |
| 3,872,856 A | 3/1975 | Clayton | |
| 3,975,350 A | 8/1976 | Hudgin et al. | |
| 4,119,094 A | 10/1978 | Micklus et al. | |
| 4,690,677 A | 9/1987 | Erb | |
| 4,763,642 A | 8/1988 | Horowitz | |
| 4,998,930 A | 3/1991 | Lundahl | |
| 5,059,166 A | 10/1991 | Fischell et al. | |
| 5,106,360 A | 4/1992 | Ishiwara et al. | |
| 5,167,622 A | 12/1992 | Muto | |
| 5,227,969 A | 7/1993 | Waggener et al. | |
| 5,259,847 A | 11/1993 | Trambert | |

(Continued)

FOREIGN PATENT DOCUMENTS

EP    0 536 440    4/1993

(Continued)

OTHER PUBLICATIONS

International Search Report of PCT/US2009/000402 mailed Apr. 15, 2009.

(Continued)

*Primary Examiner* — John Lacyk

(57) ABSTRACT

Devices and methods are provided for controlled application of a treatment to tissue adjacent a body cavity, such as after removal of tissue, e.g. cancer. A device embodying features of the invention includes one or more radiation shielding components to control emitted radiation from a radiation source to minimize radiation damage to healthy portions of the body cavity. A device embodying features of the invention can include a sealing member at a location on a shaft of the device proximal to a treatment location therein to seal the passageway leading to the body cavity. Methods for treating a body cavity include methods for delivering a radiation source to a body cavity while minimizing damaging irradiation of healthy tissue.

22 Claims, 7 Drawing Sheets

U.S. PATENT DOCUMENTS

| | | |
|---|---|---|
| 5,302,168 A | 4/1994 | Hess |
| 5,312,356 A | 5/1994 | Engelson et al. |
| 5,314,518 A | 5/1994 | Ito et al. |
| 5,342,305 A | 8/1994 | Shonk |
| 5,381,504 A | 1/1995 | Novack et al. |
| 5,411,466 A | 5/1995 | Hess |
| 5,417,687 A | 5/1995 | Nardella et al. |
| 5,428,658 A | 6/1995 | Oettinger et al. |
| 5,429,582 A | 7/1995 | Williams |
| 5,535,817 A | 7/1996 | Dunne |
| 5,566,221 A | 10/1996 | Smith et al. |
| 5,603,991 A | 2/1997 | Kupiecki et al. |
| 5,611,767 A | 3/1997 | Williams |
| 5,621,780 A | 4/1997 | Smith et al. |
| 5,653,683 A | 8/1997 | D'Andrea |
| 5,662,580 A | 9/1997 | Bradshaw et al. |
| 5,704,926 A | 1/1998 | Sutton |
| 5,720,717 A | 2/1998 | D'Andrea |
| 5,759,173 A | 6/1998 | Preissman et al. |
| 5,782,742 A | 7/1998 | Crocker et al. |
| 5,820,594 A | 10/1998 | Fontirroche et al. |
| 5,820,717 A | 10/1998 | Siegenthaler |
| 5,863,285 A | 1/1999 | Coletti |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,993,972 A | 11/1999 | Reich et al. |
| 6,022,308 A | 2/2000 | Williams |
| 6,033,357 A | 3/2000 | Ciezki et al. |
| 6,036,631 A | 3/2000 | McGrath et al. |
| 6,083,148 A | 7/2000 | Williams |
| 6,086,970 A | 7/2000 | Ren |
| 6,093,142 A | 7/2000 | Ciamacco, Jr. |
| 6,095,966 A | 8/2000 | Chornenky et al. |
| 6,143,013 A | 11/2000 | Samson et al. |
| 6,200,257 B1 | 3/2001 | Winkler |
| 6,217,565 B1 | 4/2001 | Cohen |
| 6,251,059 B1 | 6/2001 | Apple et al. |
| 6,256,529 B1 | 7/2001 | Holupka et al. |
| 6,282,142 B1 | 8/2001 | Miyawaki |
| 6,378,137 B1 | 4/2002 | Hassan et al. |
| 6,390,967 B1 | 5/2002 | Forman et al. |
| 6,390,968 B1 | 5/2002 | Harmon |
| 6,398,708 B1 | 6/2002 | Hastings et al. |
| 6,413,203 B1 | 7/2002 | Sahatjian |
| 6,413,204 B1 | 7/2002 | Winkler et al. |
| 6,416,492 B1 | 7/2002 | Nielson |
| 6,458,069 B1 | 10/2002 | Tam et al. |
| 6,482,142 B1 | 11/2002 | Winkler et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,605,030 B2 | 8/2003 | Weinberger |
| 6,610,013 B1 | 8/2003 | Fenster et al. |
| 6,615,070 B2 | 9/2003 | Lee |
| 6,673,006 B2 | 1/2004 | Winkler |
| 6,706,014 B2 | 3/2004 | Banik et al. |
| 6,723,052 B2 | 4/2004 | Mills |
| 6,746,392 B2 | 6/2004 | Stiger et al. |
| 6,752,752 B2 | 6/2004 | Geitz |
| 6,770,058 B1 | 8/2004 | Liprie |
| 6,913,600 B2 | 7/2005 | Valley et al. |
| 6,923,754 B2 | 8/2005 | Lubock |
| 6,955,641 B2 | 10/2005 | Lubock |
| 6,983,754 B1 | 1/2006 | Anderson et al. |
| 7,098,463 B2 | 8/2006 | Adamovics |
| 7,107,089 B2 | 9/2006 | Lee |
| 7,171,255 B2 | 1/2007 | Holupka et al. |
| 7,201,715 B2 | 4/2007 | Burdette et al. |
| 7,214,178 B2 | 5/2007 | Lubock |
| 7,322,929 B2 | 1/2008 | Lovoi |
| 7,404,791 B2 | 7/2008 | Linares et al. |
| 7,407,476 B2 | 8/2008 | Lubock et al. |
| 7,413,539 B2 * | 8/2008 | Lubock et al. .................... 600/3 |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,885,382 B2 | 2/2011 | Stewart et al. |
| 7,887,476 B2 | 2/2011 | Hermann et al. |
| 2001/0016725 A1 | 8/2001 | Valley et al. |
| 2001/0049464 A1 | 12/2001 | Ganz |
| 2001/0051669 A1 | 12/2001 | McGhee |
| 2002/0045893 A1 | 4/2002 | Lane et al. |
| 2002/0095114 A1 | 7/2002 | Palasis |
| 2002/0177804 A1 | 11/2002 | Saab |
| 2004/0039437 A1 | 2/2004 | Sparer et al. |
| 2004/0054366 A1 | 3/2004 | Davison et al. |
| 2004/0087827 A1 | 5/2004 | Lubock |
| 2004/0116767 A1 | 6/2004 | Lebovic et al. |
| 2004/0215048 A1 | 10/2004 | Lubock |
| 2005/0061771 A1 | 3/2005 | Murphy |
| 2005/0080313 A1 | 4/2005 | Stewart et al. |
| 2005/0124843 A1 | 6/2005 | Singh |
| 2005/0182286 A1 | 8/2005 | Lubock |
| 2005/0240073 A1 | 10/2005 | Apffelstaedt et al. |
| 2005/0240074 A1 | 10/2005 | Lubock |
| 2006/0020256 A1 | 1/2006 | Bell et al. |
| 2006/0100475 A1 | 5/2006 | White et al. |
| 2006/0116546 A1 | 6/2006 | Eng |
| 2006/0136051 A1 | 6/2006 | Furst et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2007/0005003 A1 | 1/2007 | Patterson et al. |
| 2007/0055144 A1 | 3/2007 | Neustadter et al. |
| 2007/0167666 A1 | 7/2007 | Lubock et al. |
| 2007/0270627 A1 | 11/2007 | Cutrer et al. |
| 2008/0057298 A1 | 3/2008 | Finley |
| 2008/0091055 A1 | 4/2008 | Nguyen et al. |
| 2008/0221384 A1 | 9/2008 | Chi Sing et al. |
| 2008/0221444 A1 | 9/2008 | Ritchie et al. |
| 2008/0228024 A1 | 9/2008 | Jones et al. |
| 2008/0228025 A1 | 9/2008 | Quick |
| 2008/0287801 A1 | 11/2008 | Magnin et al. |
| 2009/0171157 A1 | 7/2009 | Diederich et al. |
| 2009/0188098 A1 | 7/2009 | Acosta et al. |

FOREIGN PATENT DOCUMENTS

| | | |
|---|---|---|
| EP | 0 642 766 | 3/1995 |
| EP | 0693293 B1 | 1/1996 |
| EP | 0 719 571 | 7/1996 |
| EP | 0 853 957 | 7/1998 |
| EP | 0 867 200 | 9/1998 |
| EP | 1051990 A1 | 11/2000 |
| EP | 1070514 A1 | 1/2001 |
| EP | 1 402 922 | 3/2004 |
| EP | 1 618 924 | 1/2006 |
| RU | 2177350 C2 | 12/2001 |
| WO | WO 95/20241 | 7/1995 |
| WO | 9712540 A1 | 4/1997 |
| WO | WO 97/45053 | 12/1997 |
| WO | 9815315 A1 | 4/1998 |
| WO | 9934869 A1 | 7/1999 |
| WO | WO 01/14011 | 3/2001 |
| WO | WO 01/43826 | 6/2001 |
| WO | WO 01/58346 | 8/2001 |
| WO | WO 02/09599 | 2/2002 |
| WO | WO 02/069862 | 9/2002 |
| WO | WO 2004/043531 | 5/2004 |
| WO | WO 2005/037363 | 4/2005 |
| WO | 2005039655 A1 | 5/2005 |
| WO | 2005039665 A1 | 5/2005 |
| WO | WO 2005/067442 | 7/2005 |
| WO | WO 2007/027831 | 3/2007 |
| WO | WO 2007/143560 | 12/2007 |

OTHER PUBLICATIONS

Patent Abstracts of Japan, vol. 2000, No. 22, Mar. 9, 2001 and JP 2001 120561, May 8, 2001.

Patent Abstracts of Japan, vol. 1998, No. 10, Aug. 31, 1998, and JP 10 137250, May 26, 1998.

"Variable shield for radiation-therapy source wire and centering catheter", Research disclosure, Mason Publications, Hampshire, GB, vol. 438, No. 48, Oct. 2000, XP007126916.

Philip H. Gutin et al., "A coaxial catheter system for afterloading radioactive sources for the interstitial irradiation of brain tumors", J. Neurosurg., vol. 56., pp. 734-735, May 1982.

Gregory K. Edmundson et al., "Dosimetric Characteristics of the Mammosite RTS, a New Breast Brachytherapy Applicator", Int. J. Radiation Oncology Biol. Phys., vol. 52, No. 4, pp. 1132-1139, (2002).

Melvin A. Astrahan, Ph.D. et al., "Optimization of Mammosite Therapy", Int. J. Radiation Oncology Biol. Phys., vol. 58, No. 1, pp. 220-232, 2004.

R. D. Ashpole et al., "A New Technique of Brachytherapy for Malignant Gliomas with Caesium-137; A New Method Utilizing a Remote Afterloading system", Clinical Oncology, (1990).

Paul V. Harper, "Some Therapeutic Applications of Radioisotopes", *Journal of the Mississippi State Medical Association*, Oct. 1966, vol. VII, pp. 526-533.

Cuttino, L. W., et al., "CT-Guided Multi-Catheter Insertion Technique for Partial Breast Brachytherapy: Reliable Target Coverage and Dose Homogeneity", Brachytherapy 4, 2005, pp. 10-17, Elsevier.

Glasgow, G. P., et al. "Remote Afterloading Technology", AAPM Report No. 41, 1993, pp. i-vi and 1-107, American Institute of Physics, Inc.

Hoshino, T., "Brian Tumor Research Center", Abstracts of the 11th Conference On Brain Tumor Research and Therapy, Journal Of Neuro-Oncology 28, 1996, pp. 31-113.

Abstracts of the 11th International Conference on Brain tumor Research and Therapy Oct. 31-Nov. 3, 1995, Silverado Country Club and Resort, Napa, California, Journal of Neuro-Oncology 28:72, 1996.

Johannesen, T.B. et al, "Intracavity Fractioned Balloon Brachytherapy in Glioblastoma", Acta Neurochir (Wien) (1999) 141: 127-133.

Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.

Devic, et al., "Advantages of Inflatable Multichannel Endorectal Applicator In The Neo-Adjuvant Treatment of Patients With Locally Advanced Rectal Cancer With HDR Brachytherapy", Journal Of Applied Clinical Medical Physics, Spring 2005, pp. 44-49, vol. 6, No. 2.

Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.

Friedman, M, et al., "A New Technic For the Radium Treatment Of Carcinoma Of The Bladder", Presented at the Thirty-fourth Annual Meeting of the Radiological Society of North America, Dec. 5-10, 1948, pp. 342-362.

Walton, R. J., "Therapeutic Uses of Radioactive Isotopes In The Royal Cancer Hospital", The British Journal of Radiology, 1950, pp. 559-599, William Heinemann, Publisher.

Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.

Low-Beer, B. V. A., "The Therapeutic Use Of Radioactive Isotopes", "Practical Therapeutics", Dec. 1954, pp. 69-87, vol. X, No. 6.

Muller, J. H., "Radiotherapy Of Bladder Cancer By Means Of Rubber Balloons Filled In Situ With solutions of A Radioactive Isotopr (Co60)", Cancer, A Journal of the American Cancer Society, Jul.-Aug. 1955, pp. 1035-1043, Vol. 8, No. 4, J. B. Lippincott Company, Philadelphia.

Friedman, M, et al., "Irradiation Of Carcinoma Of The Bladder By A Central Intracavitary Radium Or Cobalt 60 Source (The Walter Reed Technique)", Presented at the Annual Meeting of the American Radium Society, 1955, pp. 6-31.

Hewitt, C. B., et al., "Update On Intracavitary Radiation In The Treatment Of Bladder Tumors", The Journal Of Urology; Official Journal Of The American Urological Association, Inc., 1981, pp. 323-325, vol. 126 September, The Williams & Wilkins Co.

Hieshima,G. B., et al. "A Detachable Balloon for Therapeutic Transcatheter Occlusions 1", Technical Notes, Jan. 1981, pp. 227-228, vol. 138.

Russel, A. H., et al, "Intracavitary Irradiation For Carcinoma Of The Urinary Bladder: Rationale, Technique, And Preliminary Results", Int. J. Radiation Oncology. Phys,. 1984, pp. 215-219, vol. 10, Pergamon Press Ltd.

Yin, W., "Brachytherapy of Carcinoma of the Esophagus in China, 1970-1974 and 1982-1984", Brachytherapy HDR And LDR, May 4-6, 1989, pp. 52-56.

Kaufman, N., "Remote Afterloading Intraluminal Brachytherapy In The Treatment Of Rectal, Rectosigmoid, and Anal Cancer: A Feasibility Study", International Journal Of Radiation Oncology, Biology, Physics Sep. 1989, pp. 663-668, vol. 17, Issue 3, Pergamon Press plc.

Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.

Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.

Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.

Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.

Micheletti, E., et al., "High-Dose-Rate Brachytherapy for Poor-Prognosis, High-Grade Glioma: (Phase II) Preliminary Results", Tumori, 1996, pp. 339-344.

Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.

Nag, S., et al., "Remote Controlled High Dose Rate Brachytherapy", Critical Reviews in Oncology/Hematology 22, 1996, pp. 127-150, Elsevier Science Ireland Ltd.

Sylvester, J., et al., "Interstitial Implantation Techniques in Prostate Cancer" Journal of Surgical Oncology 1997; 66: 65-75, Wiley-Liss, Inc.

Tan, L. T., et al., Radical Radiotherapy for Carcinoma of the Uterine Cervix Using External Beam Radiotherapy and A Single Line Source Brachytherapy Technique: The Clatterbridge Technique, The British Journal of Radiology, 70, date Dec. 1997, pp. 1252-1258.

Kuettel, M. R., et al., "Treatment of Female Urethral Carcinoma In Medically Inoperable Patients Using External Beam Irradiation and High Dose Rate Intracavitary Brachytherapy" The Journal of Urology, May 1997, pp. 1669-1671, vol. 157, The American Urological Association, Inc.

Slevin, N. J., et al., "Intracavitary Radiotherapy Boosting for Nasopharynx Cancer" The British Journal of Radiology, 70, Apr. 1997, pp. 412-414.

Sneed, P, K., et al., Interstitial Brachytherapy Procedures for Brain Tumors, Seminars in Surgical Oncology 1997; 13: 157-166, Wiley-Liss, Inc.

Dempsey, J. F., et al., "Dosimetric Properties of a Novel Brachytherapy Balloon Applicator For The Treatment Of Malignant Brain-Tumor Resection-Cavity Margins" Int. J. Radiation Oncology Biol. Phys., May 1998, pp. 421-429, vol. 42, No. 2, Elsevier.

Kolotas, C., et al., "CT Guided Interstitial High Dose Rate Brachytherapy For Recurrent Malignant Gliomas", The British Journal Of Radiology, 72, (1999), pp. 805-808.

Demanes, D, J., et al., "The Use And Advantages Of A Multichannel Vaginal Cylinder in High-Dose-Rate Brachytherapy", Int. J. Radiation Oncology Biol. Phys., (1999), pp. 211-219, vol. 44, No. 1, Elsevier Science Inc.

Debicki, M. P., et al., "Localization Current Field Hyperthermia In Carcinoma of The Cervix: 3-D Computer Simulation Of SAR Distribution", International Journal Of Hyperthermia, 1999, pp. 427-440, vol. 15, No. 5.

Garipagaoglu, M, et al., "Geometric and Dosimetric Variations of ICRU Bladder And Rectum Reference Points In Vaginal Cuff Brachytherapy Using Ovoids", Int. J. Radiation Oncology Biol. Phys. 2004, pp. 1607-1615, Elsevier Inc.

Bowsher, W. G., et al., "Update on Urology-Prostate Cancer, 4-Treatment of Local Disease", European Journal Of Surgical Oncology, 1995 pp., 679-682, vol. 21, No. 6.

Voung, T, et al., "High-Dose-Rate Endorectal Brachytherapy In the Treatment Of Loacally Advanced Rectal Carcinoma: Technical Aspects", Brachytherapy 4, 2005, pp. 230-235, Elsevier Inc.

Harada, T, et al., "Transcystoscopic Intracavitary irradiation For Carcinoma Of The Bladder: Technique and Preliminary Clinical Results", The Journal of Urology, Oct. 1987, pp. 771-774, vol. 138, No. 4, The Williams & Wilkins Co.

Hall, J. W., et al., "Histologic Changes in Squamous-Cell Carcinoma of The Mouth and Oropharynx Produced by Fractionated External Roentgen Irradiation", Radiological Society of North America, 1948, pp. 318-350, 50/3/MAR.

Hine, G. J., et al., "Isodose Measurements Of Linear Radium Sources In Air And Water By Means Of An Automatic Isodose Recorder", The American Journal of Roentgenology and Radium Therapy, 1950, pp. 989-998, vol. 64, No. 6, The Societies.

Walton, R. J., et al., Radioactive Solution (24Na and 82 Br) In the Treatment Of Carcinoma Of The Bladder:, British Medical Bulletin, 1952, pp. 158-165, Medical Dept., The British Council.

Marshall V. F., et al., "Current Clinical Problems Regarding Bladder Tumors", Symposium On Bladder Tumors, 1956, pp. 543-550, 9/3/ May-Jun., J. B. Lippincott Co, Etc.

Hewitt, C. B., et al., "Intracavitary Radiation In The Treatment Of Bladder Tumors", The Journal Of Urology, vol. 107, Apr. 1972, pp. 603-606, The Williams & Wilkins Co.

Rotman, M., et al., "The Intracavitary Applicator In Relation To Complications Of Pelvic Radiation-The Ernst System", Int. J. Radiation Oncology Biol. Phys., 1978, pp. 951-956, vol. 4, Pergamon Press Inc.

Nag, S., et al., "The Future Of High Dose Rate Brachytherapy", High Dose Rate Brachytherapy: A Textbook, 1994, pp. 447-453, Futura Publishing Company, Inc. , Armonk, New York 10504.

Wang, C. C., "Carcinoma Of The Nasopharynx", Radiation Therapy Of Head and Neck Neoplasms, 1997, pp. 257-280, Chapter 10, Wiley-Liss, Inc.

Gaspar, L. E., et al., "Esophageal Brachytherapy", Principles And Practice Of Brachytherapy, 1997, pp. 305-321, Futrua Publishing Company, Inc., Armouk, New York.

Vicini, F. A., et al, "Dose-Volume Analysis For Quality Assurance Of Interstitial Brachytherapy For Breast Cancer", Int. J. Radiation Oncology Biol. Phys., vol. 45, 1999, pp. 803-810, Elsevier Science Inc.

Akagi, Y, et al., "Optimum Fractionation For High-Dose-Rate Endoesophageal Brachytherapy Following External Irradiation Of Early State Esophageal Cancer", Int. J. Radiation Oncology Biol. Phys., vol. 43, 1999, pp. 525-530, Elsevier Science, Inc.

Xu, Z., et al., "Calculation of Dose Distribution Near An Innovative Concentric Balloon Catheter For Endovascular Brachytherapy", Cardiovascular Radiation Medicine 2, 2000, pp. 26-31, Elsevier Science Inc.

Stubbs, J. B., et al., "Preclinical Evaluation Of A Novel Device For Delivering Brachytherapy To The Margins Of Resected Brain Tumor Cavities", J. Neurosurg 96, Feb. 2002, pp. 335-343, vol. 96.

Das, R. K., et al., "3D-CT-Based High-Dose-Rate Breast Brachytherapy Implants: Treatment Planning And Quality Assurance", Int. J. Radiation Oncology Biol. Phys. 2004, pp. 1224-1228, vol. 59, No. 4, Elsevier Inc.

* cited by examiner

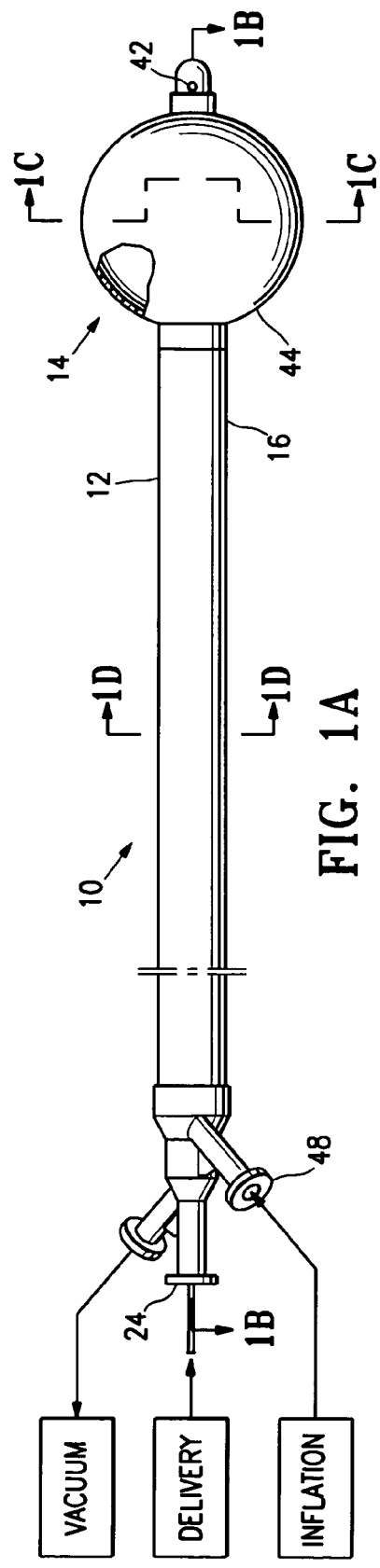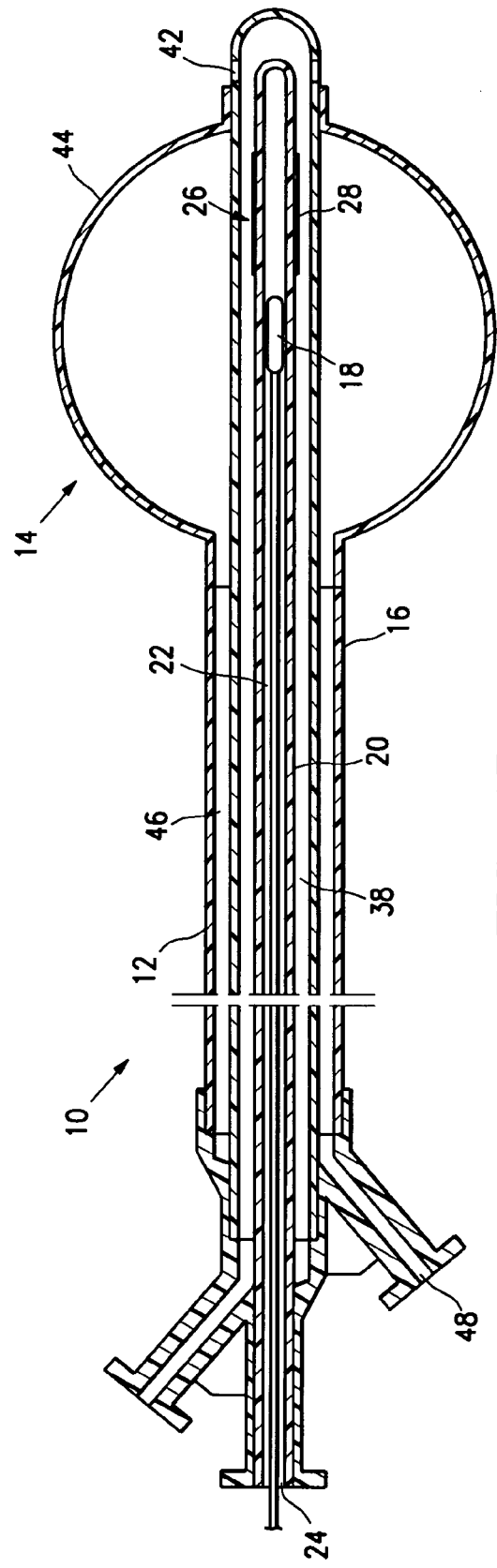

TREATMENT OF A BODY CAVITY

RELATED APPLICATIONS

This application is a divisional of application Ser. No. 11/283,236, filed Nov. 18, 2005, now U.S. Pat. No. 7,413,539, which is incorporated herein in its entirety by reference and from which priority is claimed.

FIELD OF THE INVENTION

This invention relates generally to the fields of medical treatment devices and methods. In particular, the invention relates to devices and methods for treating tissue surrounding a body cavity, such as a site from which cancerous, precancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Iotrex®, Proxima Therapeutics, Inc.). A radiation source such as a miniature or microminature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when only the portion of tissue requiring treatment receives the radiation and where surrounding healthy tissue is unaffected. Tissue cavities typically are not uniform or regular in their sizes and shapes, so that differences in dosages applied to different regions of surrounding tissue, including "hot spots" and regions of relatively low dosage, often result from radiation treatment.

A treatment delivery device for treating tissue adjacent a body cavity has been disclosed in U.S. Pat. No. 6,923,754. This device applies a partial-vacuum or suction to bring tissue towards a radiation source and allows for uniform application of radiation to tissue surrounding a body cavity. An advantage of the present invention is that it allows for the protection of healthy tissue within that body cavity and provides a seal in the passageway leading to the body cavity while treating the desired tissue.

SUMMARY OF THE INVENTION

This invention is generally directed to treating a patient's body cavity, such as by irradiation, and devices and methods for such treatments. The invention is particularly suitable for treating tissue adjacent a patient's body cavity formed by removal of tissue for a biopsy.

More specifically, a device embodying features of the invention includes an elongate shaft with a treatment location at a distal portion of the shaft which is configured to receive or which includes a source for a treatment agent, such as a radiation source. In this embodiment the device has one or more radiation shielding components that control at least in part the radiation emitted from the radiation source.

The radiation shielding component is designed to reduce or minimize damaging irradiation of healthy tissue surrounding the body cavity while treating nearby areas having diseased tissue with radiation emitted from the radiation source. The radiation shielding components include one or more radiation shields disposed about a delivery shaft containing the radiation source. Preferably, the radiation shielding component has a pair of radiation shields one that is deployed proximal and one that is deployed distal to the treatment location to control axial and near axial radiation emissions of the radiation source. The location of the pair of radiation shields is configured to be adjustable to accommodate anatomical structural variations or to adjust treatment parameters. A central radiation shield preferably has or defines at least in part a window to control the dispersal of radiation from a radiation source. The window defined at least in part by the central radiation shield has a length between about 2 millimeters and 5 centimeters. The shielded area of the central radiation shield is arcuate with an angular range from about 20° to about 240°. While the central radiation shield may be utilized by itself, preferably, the central radiation shield is configured to be deployed between the proximal and distal shields such as discussed above.

A device embodying features of another aspect of the invention includes an elongate shaft with a sealing member located on the elongate shaft proximal to the treatment location to seal the intracorporal passageway through which the device is advanced. The sealing member is expanded or expandable and configured to minimize the loss of vacuum within the body cavity when a vacuum is developed therein. Preferably the sealing member is also configured to seal the passageway when aspirating fluid from the body cavity or delivering fluid, e.g. treatment fluid, to the body cavity.

A device embodying features of the invention preferably has an enlarged or enlargeable cavity filling member at the treatment location which at least in part fills the body cavity. Preferably the cavity filling member is inflatable such as a balloon. The device also includes an inner lumen configured to be in fluid communication with a proximal vacuum source and one or more vacuum ports preferably proximal and or distal to the cavity filling member such as described in U.S. Pat. No. 6,923,754 and co-pending application Ser. No. 10/849,410 filed on May 19, 2004, both of which are assigned to the present assignee. Application of a vacuum within the inner lumen aspirates fluid in the cavity through one or more vacuum ports and the vacuum within the body cavity pulls tissue defining the cavity onto the exterior of the cavity filling member deployed within the cavity.

Methods for treating a body cavity of a patient include methods for delivering a source for a treatment agent such as a radiation source to a body cavity to treat the desired tissue while minimizing damaging irradiation of healthy tissues. More specifically, a method for treating a body cavity includes providing a device having an elongate shaft with a proximal end, a distal end, and a treatment location in a distal portion of the shaft. The method further includes providing a radiation source configured to be deposited in the treatment location and a radiation shielding component configured to control at least in part the emission of radiation emitted from the treatment location. The device is inserted into a body cavity and the radiation source is positioned within the treatment location. The radiation shielding component is positioned to shield portions of the body cavity from radiation emitted from the radiation source.

Enhanced control over the emission of radiation from a radiation source and an improved seal in the passageway leading to the body cavity are provided by the present invention. These and other advantages of the present invention are described in more detail in the following written description and the accompanying exemplary drawings.

BRIEF DESCRIPTION OF THE DRAWINGS

FIG. 1A is a schematic view of a device embodying features of the invention including a cavity filling member.

FIG. 1B is a longitudinal cross sectional view of the device along lines 1B-1B in FIG. 1A.

DETAILED DESCRIPTION OF THE INVENTION

Figure 1D:
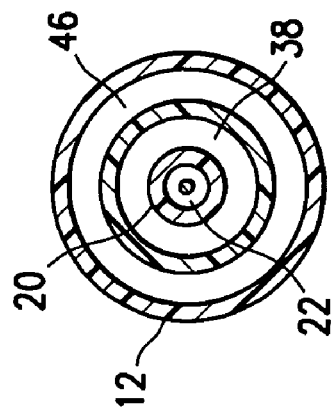
FIG. 1D is a transverse cross sectional view of the device taken along lines 1D-1D.
Figure 1C:
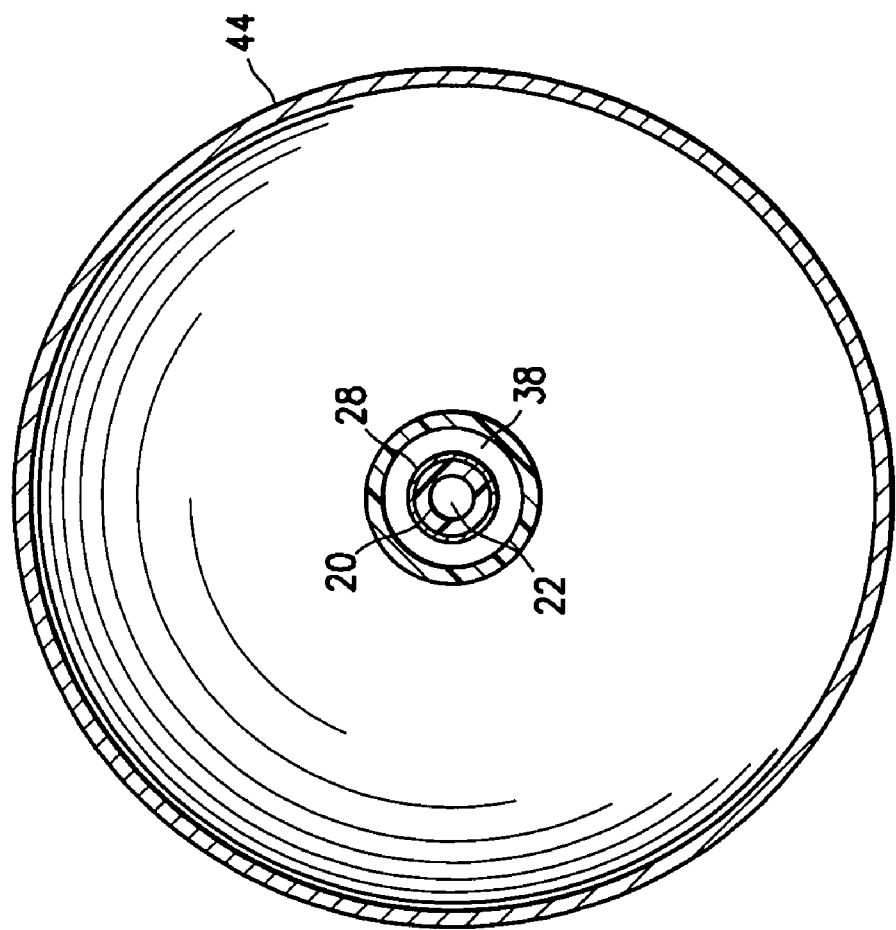
FIG. 1C is a transverse cross sectional view of the device taken along lines 1C-1C in FIG. 1A.

The present invention provides devices and methods for treatment of a patient's body cavity. For example, devices and methods having features of the invention are used to deliver radiation or other treatment into a biopsy site or into a cavity left after removal of cancerous tissue from the patient's body.

As shown in FIGS. 1A-1D a device 10 embodying features of the invention includes an elongated shaft 12 with a treatment location 14 in a distal portion 16 of the elongate shaft 12. The treatment location 14 includes a source for a treatment agent such as a radiation source 18. The elongate shaft 12 contains a delivery shaft 20 having a delivery lumen 22. The delivery shaft 20 also includes a delivery port 24 through which the radiation source 18 is advanced. The device 10 has one or more radiation shielding components 26 disposed about the delivery shaft 20 that control in part the radiation emitted from the radiation source 18. The radiation shielding component 26 is designed to reduce or minimize damaging irradiation of healthy tissue surrounding a body cavity while treating nearby areas having diseased tissue with radiation emitted from the radiation source 18.

Figure 2A:
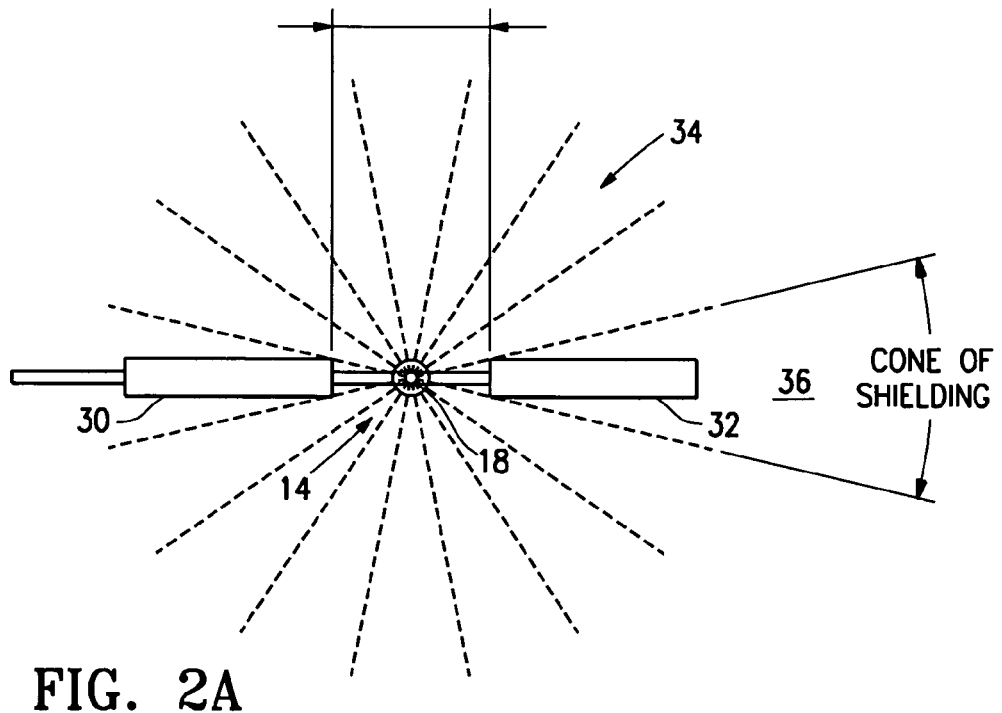
FIGS. 2A and 2B are diagrammatic views of a radiation shielding component which includes a proximal radiation shield and a distal radiation shield.
Figure 2B:
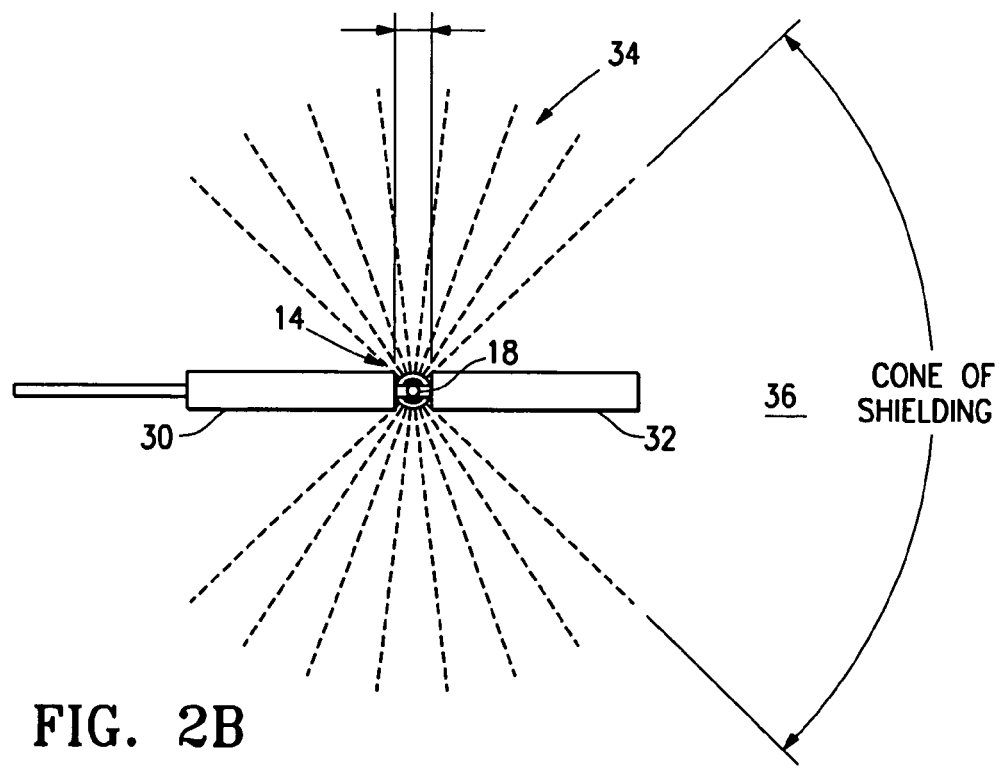

The radiation shielding component 26 includes at least one radiation shield 28 which is configured to be deployed proximal to, distal to, or within the treatment location 14. Preferably, the radiation shielding component 26 has a pair of radiation shields including a proximal radiation shield 30 and a distal radiation shield 32 (FIGS. 2A-2B). The proximal shield 30 is deployed proximal to the treatment location 14 and the distal shield 32 is deployed distal to the treatment location 14. The shields allow for control, at least in part, of the axial and near axial emissions from the proximal and distal end portions of the elongate shaft 12. When the proximal end of distal radiation shield 32 is adjacent the radiation source 18 and the distal end of the proximal radiation shield 30 is adjacent the radiation source 18 the radiation dispersal pattern 34 would be a small cone emanating from the radiation source 18. As the proximal end of the distal radiation shield 32 and the distal end of the proximal radiation shield 30 move further away from the radiation source 18 the radiation dispersal pattern 34 increases to a near spherical shape having an axial cone of shielding 36 expanding from the radiation source 18 along the longitudinal axis in both directions. The pair of radiation shields 30 and 32 are preferably configured to be adjustable to accommodate anatomical structural variations or to adjust treatment parameters.

The radiation shielding component 26 includes one or more radiation shields 28. The radiation shields 28 are formed of a suitably radiopaque metal or polymer containing at least in part a radiation absorbing material and are preferably tubular. The shields are preferably slidably disposed about the delivery lumen 22 of the device 10. Suitable radiation absorbing materials include tantalum, bismuth subcarbonate, barium sulfate, platinum, gold and tungsten.

The radiation source 18 of the device 10 can include a radiation source which is solid or liquid. Suitable liquid radiation sources include, for example, a liquid containing a radioactive iodine isotope (e.g., $I^{125}$ or $I^{131}$), a slurry of a solid isotope, for example, $^{198}AU$ or $^{169}Yb$, or a gel containing a radioactive isotope. Liquid radiation sources are commercially available (e.g., Iotrex®, Proxima Therapeutics, Inc., Alpharetta, Ga.). The radiation source 18 preferably includes brachytherapy seeds or other solid radiation sources used in radiation therapy, for example, a radioactive microsphere available from 3M company of St. Paul, Minn. The radiation source 18 is either preloaded into the device 10 at the time of manufacture or is loaded into the device 10 after placement into a body cavity of a patient. Solid radionuclides suitable for use with a device 10 embodying features of the present invention are currently generally available as brachytherapy radiation sources (e.g., I-Plant™, Med-Tec, Orange City, Iowa.). Radiation may also be delivered by a device such as the x-ray tube of U.S. Pat. No. 6,319,188. The x-ray tubes are small, flexible and are believed to be capable of being maneuverable enough to reach the desired location within a patient's body.

One embodiment of the device 10 also includes a vacuum lumen 38. The vacuum lumen 38 is configured to be in fluid communication with a vacuum source and one or more vacuum ports 42 in the exterior of the elongated shaft 12. The vacuum ports 42 are in fluid communication with the vacuum lumen 38 to provide a vacuum within a body cavity.

In one embodiment the device 10 includes a cavity filling member 44 which at least in part fills the body cavity located on the distal portion 16 of the elongated shaft 12. The cavity filling member 44 can be inflatable or expandable and configured to contact tissue surfaces defining the body cavity. The cavity filling member 44 is in fluid communication with a first inflation lumen 46 which has a first inflation port 48. The vacuum ports 42 for the vacuum lumen 38 preferably are located proximal and or distal to the cavity filling member 44 which at least partially fills the body cavity.

Figure 3A:
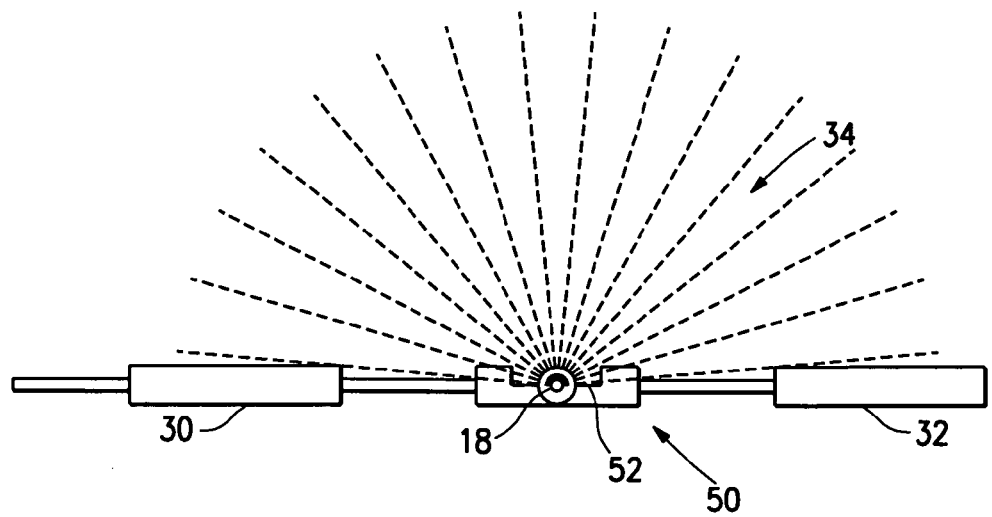
FIG. 3A is a diagrammatic view of a central radiation shield disposed about a radiation source.
Figure 3B:
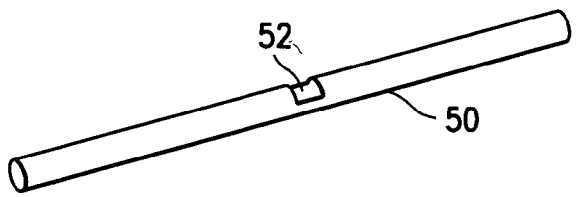
FIG. 3B is a perspective view and FIG. 3C is an elevational view of a central radiation shield including a window.
Figure 3D:
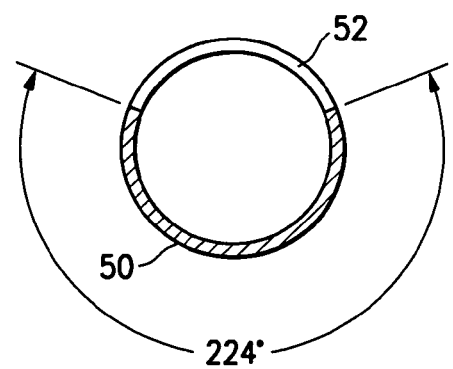
FIG. 3D is a transverse cross sectional view of the central radiation shield taken along lines 3D-3D in FIG. 3C.
Figure 3C:
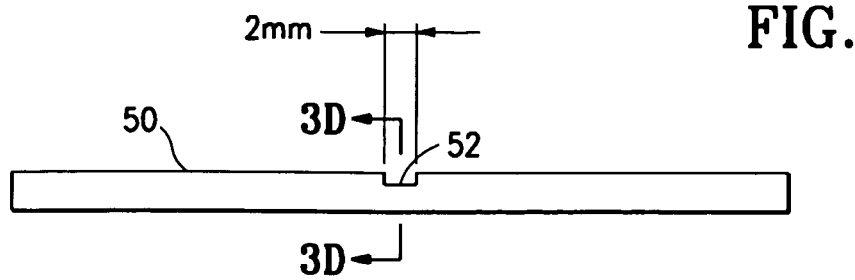
Figure 3E:
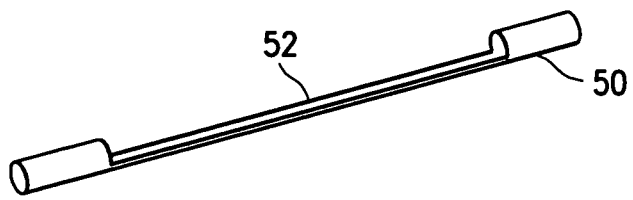
FIG. 3E is a perspective view and FIG. 3F is an elevational view of a central radiation shield including a window.
Figure 3G:
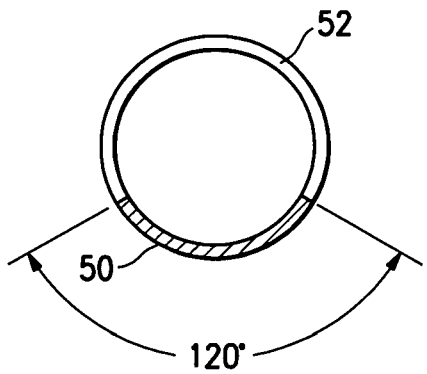
FIG. 3G is a transverse cross sectional view of the central radiation shield taken along lines 3G-3G in FIG. 3F.
Figure 3F:
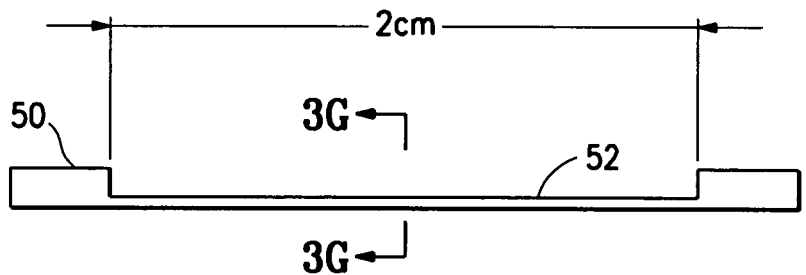

A central radiation shield 50, shown in FIG. 3A, can be deployed between the proximal 30 and distal 32 radiation shields. The central radiation shield 50 preferably defines at least in part a window 52 to allow for dispersal of radiation from a radiation source 18. Preferably the central radiation shield 50 defines a window 52 which may have a variable length as shown in FIGS. 3B-G. Preferably the length of the window 52 is between about 2 millimeters to 5 centimeters and the central radiation shield is tubular in shape. Preferably the shielded area is arcuate with an angular range from about 20° to about 240°. Alternatively the central radiation shield 50 comprises a pair of separately rotatable members to allow for adjusting the window dimensions. The central radiation shield 50 is rotated or advanced to position the window 52 near the target tissue.

Figure 4A:
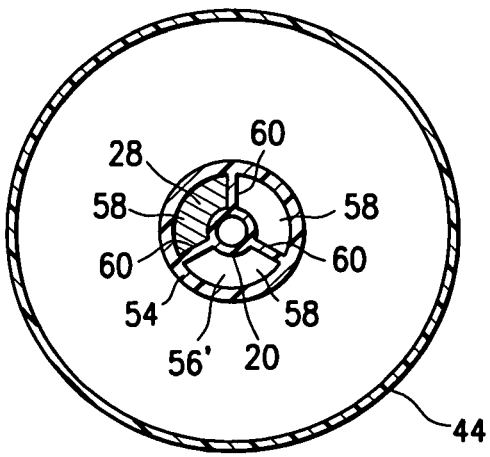
FIGS. 4A and 4B are transverse cross sectional views of an embodiment of the invention including three chambers, some of which contain radiation shields.
Figure 4B:
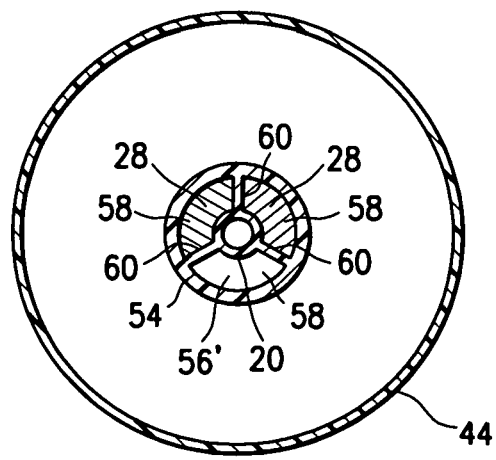

Another embodiment of the invention shown in FIGS. 4A and 4B includes a partitioned shaft 54 disposed about the delivery shaft 20. The partitioned shaft 54 has a lumen 56 which is divided into at least two chambers 58 by spacing elements 60. Radiation shields 28 are configured to be inserted into one or more chambers 58 through the proximal end of the elongate shaft 12 to surround at least a portion of the treatment location 14. The radiation shields 28 reduce or minimize irradiation of healthy portions of the body cavity while treating nearby areas with the radiation source 18.

In one possible embodiment the radiation shield 28 has varying densities acting as a filter to allow for some controlled amount of radiation to pass through yielding a non-symmetric radiation dosing. In another embodiment the radiation shields 28 are constructed of sintered metal to block radiation and still allow for a fluid pathway for suction or vacuum of the body cavity.

Figure 5A:
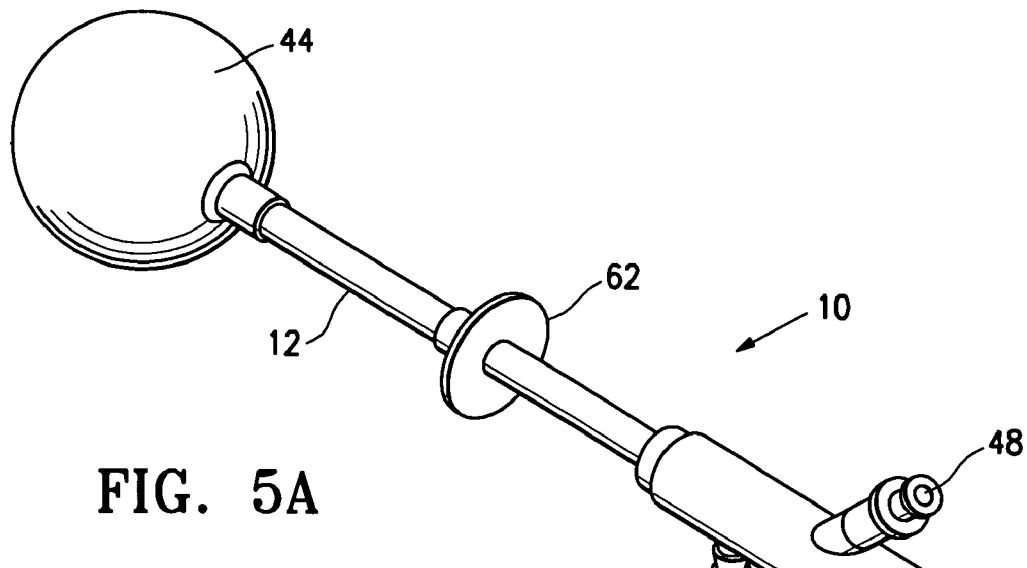
FIG. 5A is perspective view of a device embodying features of the invention including a sealing member which is formed of an adhesive material.
Figure 5B:
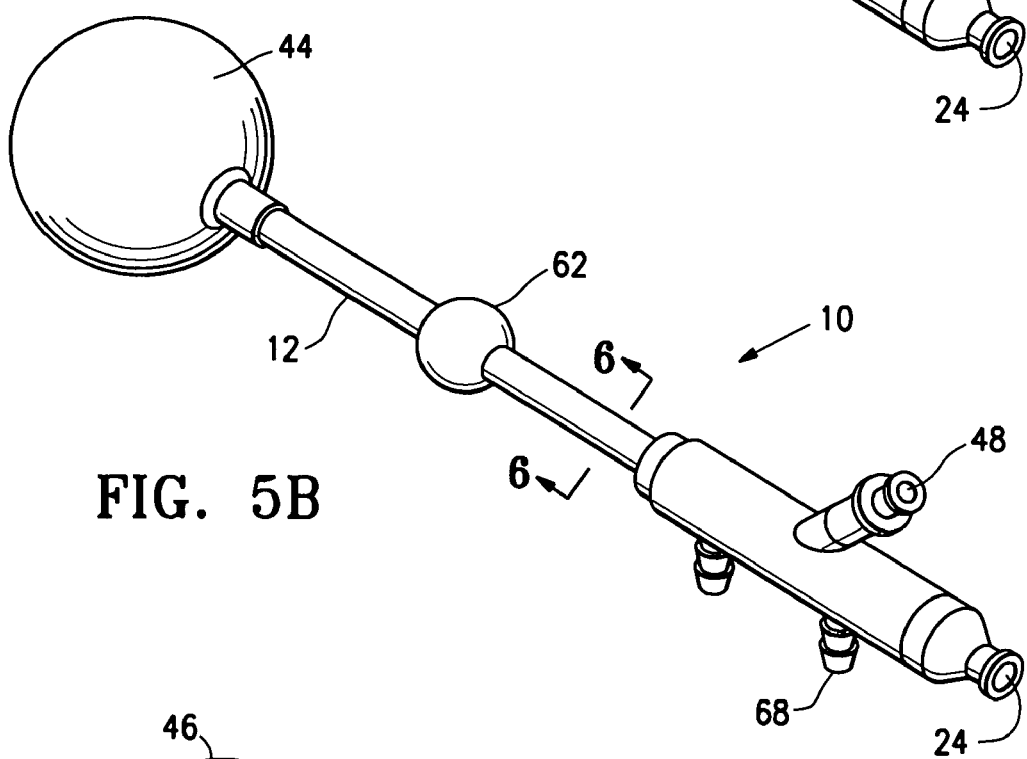
FIG. 5B is a perspective view of a device embodying features of the invention including an sealing member which is inflatable.
Figure 6:
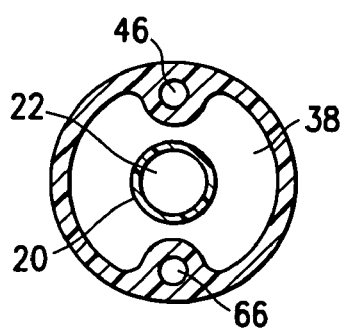
FIG. 6 is a cross sectional view of the device taken along line 6-6 in FIG. 5B.

In another embodiment of the invention depicted in FIGS. 5A, 5B and 6 the device includes an elongate shaft 12 with a sealing member 62 located on the elongate shaft 12 to seal the passageway 64 through which the device 10 is advanced. The sealing member can be inflated via a second inflation lumen 66 (FIGS. 5B and 6A) which is in fluid communication with a second inflation port 68 on the proximal end of the elongate shaft 12. The sealing member 62 allows for closer contact with the walls of the passageway 64. Preferably, the device 10 also includes a cavity filling member 44 which at least in part fills the body cavity and which is inflatable or expandable. The sealing member 62 is located on the elongate shaft 12 proximal to the distal end of the elongate shaft.

Alternatively, as shown in FIG. 5A, the device 10 can include a sealing member 62 formed of a flange or cuff having an adhesive distal face and located toward the proximal end of the elongate shaft 12. The sealing member 62 preferably is configured to form a seal in the passageway 64 leading to the body cavity by adhering to a patient's skin.

The device 10 preferably includes a vacuum lumen 38 configured to be in fluid communication with a proximal vacuum source and one or more vacuum ports 42 preferably proximal and or distal to the cavity filling member 44. Application of a vacuum within the vacuum lumen 38 aspirates fluid in the cavity through one or more vacuum ports 42 and pulls tissue defining the cavity onto the exterior of the cavity filling member 44 deployed within the cavity. As shown in FIG. 5B the sealing member 62 preferably is expanded or expandable, such as a balloon, and configured to minimize the loss of vacuum within the body cavity when a vacuum is developed.

A device 10 having features of the invention can include contoured pads for use on the elongate shaft 12 of the device 10. The contoured pads are provided on the proximal portion of the elongated shaft 12 of the device 10 and are configured to cover a portion of the shaft. The contoured pads preferably are comprised of material having soft tapered edges to minimize irritation to the skin caused by movement or dressing and undressing. The pads are taped externally to the patient or alternatively are attached to the patient with a double sided tape or adhesive material.

A device 10 having features of the invention can be provided, at least in part, with a lubricious coating, such as a hydrophilic material. The lubricious coating preferably is applied to the elongate shaft 12 or to the cavity filling member 44, if one is present, to reduce sticking and friction during insertion of a device 10. Hydrophilic coatings such as those provided by AST, Surmodics, TUA Systems, Hydromer, or STS Biopolymers are suitable.

A device 10 having features of the invention may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating preferably is be comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating is provided on the elongated shaft of the delivery device 10 at the point where the device 10 enters the skin.

Figure 7A:
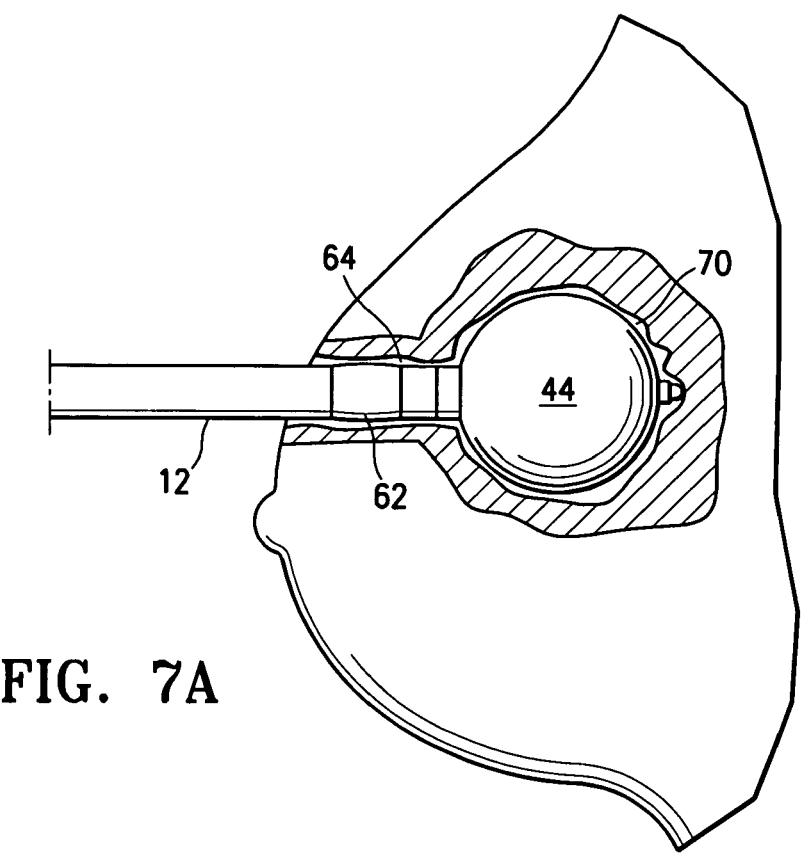
FIGS. 7A and 7B show the steps of a preferred method for treating a body cavity.
Figure 7B:
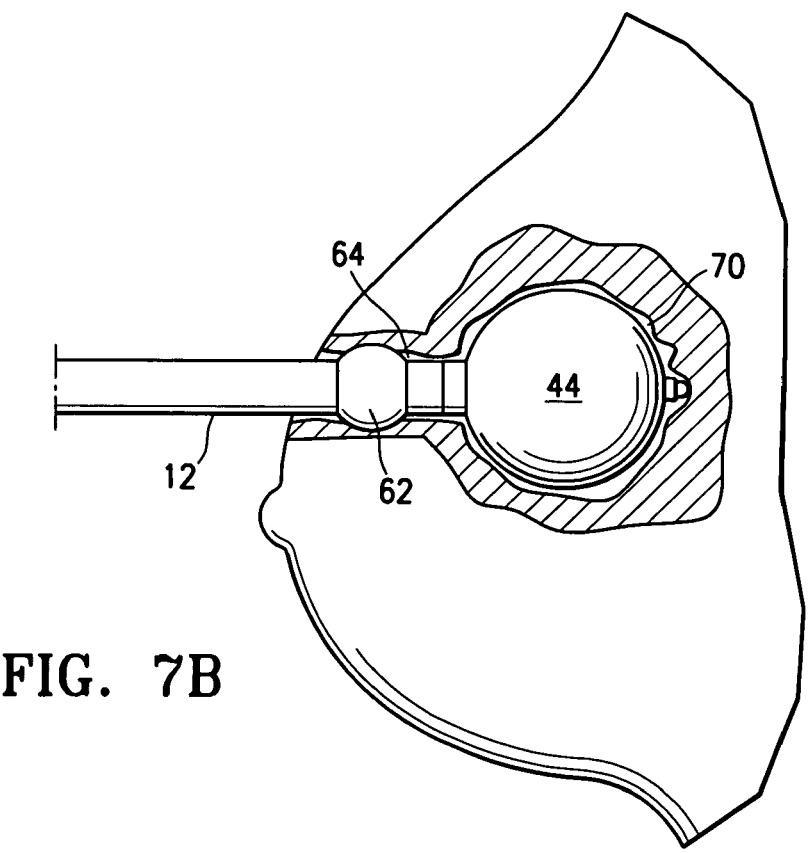

Methods for treating a body cavity 70 of a patient, shown in FIGS. 7A and 7B, include delivering a radiation source 18 to a body cavity 70 to treat the desired tissue adjacent a device 10 embodying features of the invention while minimizing damaging irradiation of healthy tissue. For example, a method of treating tissue adjacent a body cavity 70 includes inserting a device 10 embodying features of the invention into the body cavity 70, positioning a radiation shielding component 26 to shield healthy tissue in the body cavity 70 and positioning a source for a treatment agent, such as radiation source 18 within the treatment location 14 in a distal portion 16 of the shaft 12.

Methods for treating tissue adjacent a body cavity 70 include methods for sealing a passageway 64 leading to a body cavity 70. For example, a method of treating tissue adjacent a body cavity 70 includes inserting a device 10 embodying features of the invention into the body cavity 70 and sealing the passageway 64 leading to the body cavity 70 (FIG. 7A) and then at least in part contacting the passageway 64 with a sealing member 62 on the elongate shaft 12 (FIG. 7B).

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means" or "step" followed by a particular function without reference to a specific structure or action. All patents and all patent applications referred to above are hereby incorporated by reference in their entirety.

What is claimed is:

1. A method for treating a cavity of a patient's body, comprising:
    a.) providing a device having an elongate shaft with a proximal end, a distal end, a treatment location at a distal portion of the shaft and a cavity filling member surrounding the treatment location which has a tissue contacting exterior surface;
    b.) providing a radiation shielding component which is configured to control at least in part the emission of radiation emitted from a radiation source within the treatment location;
    c.) inserting the device into the patient's body and advancing the device through a passageway therein until the cavity filling member is disposed within the cavity;
    d.) applying a vacuum within the cavity to conform tissue surrounding the cavity to the tissue contacting exterior surface of the cavity filling member;
    e.) positioning advancing the radiation source through the elongated shaft until the source is disposed within the treatment location; and
    f.) adjusting the position of the radiation shielding component within the treatment location to shield portions of the tissue surrounding the cavity from radiation emitted from the radiation source.

2. A method of treating a cavity of a patient's body comprising:
    a.) providing a device having an elongate shaft with a proximal end, a distal end, a treatment location at a distal portion of the shaft, a cavity filling member having a tissue contacting outer surface and surrounding the treatment location and a sealing member on the elongated shaft proximal to the cavity filling member;
    b.) providing a source for a treatment agent configured to be disposed;
    c.) inserting the device into the patient's body and advancing the device through a passageway therein until the cavity filling member is disposed within the cavity and the sealing member is disposed within the passageway;
    d.) applying a vacuum within the cavity to conform tissue surrounding the cavity to the tissue contacting exterior surface of the cavity filling member;
    e.) sealing the passageway leading to the cavity with the sealing member disposed within the passageway; and
    f.) advancing a treatment agent to the treatment location to treat tissue surrounding the cavity.

3. The method of claim 2 wherein the sealing member is expanded to seal the passageway.

4. The method of claim 2 wherein the sealing member is inflatable and inflation fluid is injected into the sealing member to expand the sealing member.

5. The method of claim 2 wherein the treatment agent is a radiation source.

6. The method of claim 5 wherein the radiation source is a brachytherapy seed.

7. The method of claim 5 wherein the radiation source is selected from the group consisting of a liquid containing a radioactive iodine isotope, a slurry of solid isotope, a gel containing a radioactive isotope solid, or a microminiature x-ray tube.

8. The method of claim 2 wherein the sealing member within the passageway maintains a vacuum within the cavity for an effective length of time.

9. The method of claim 1 wherein the cavity filling member is inflated to partially fill the cavity and a vacuum is applied to the cavity to conform tissue surrounding the cavity to the tissue contacting surface of the inflated cavity filling member.

10. The method of claim 1 wherein the device has at least one vacuum port proximal or distal to the cavity filling member and a vacuum is formed in the cavity through the vacuum port in the device.

11. The method of claim 1 wherein the radiation shielding component is slidably disposed within a lumen in the elongate shaft.

12. The method of claim 1 wherein the radiation shielding component is deployed proximal to a radiation source in the treatment location.

13. The method of claim 1 wherein the radiation shielding component is deployed distal to a radiation source in the treatment location.

14. The method of claim 1 wherein the radiation source is a solid material.

15. The method of claim 14 wherein the radiation source is a brachytherapy seed.

16. The method of claim 1 wherein the radiation source is selected from the group consisting of a liquid containing a radioactive iodine isotope, a slurry of solid isotope, a gel containing a radioactive isotope solid, or a microminiature x-ray tube.

17. The method of claim 1 wherein the radiation shielding component is slidably advanced within the elongate shaft until it is deployed in the treatment location.

18. The method of claim 17 wherein the radiation shielding component defines in part a window.

19. The method of claim 18 wherein the length of the window is about 2 millimeters to about 5 centimeters.

20. The method of claim 18 wherein the radiation shielding component has an arcuate shielded area with an angular range between about 20° to about 240°.

21. The method of claim 1 wherein the radiation shielding component has a first portion configured to be deployed distal to the radiation source in the treatment location and a second portion configured to be deployed proximal to the radiation source in the treatment location.

22. The method of claim 21 wherein spacing between the first and second portion of the radiation shield component are adjusted.

* * * * *